United States Patent [19]
Talmadge

[11] Patent Number: 5,912,232
[45] Date of Patent: Jun. 15, 1999

[54] ANTI-INFLAMMATORY POLYPEPTIDE ANTAGONISTS OF HUMAN Il-8

[75] Inventor: James E. Talmadge, Bellevue, Nebr.

[73] Assignee: Board of Regents of the University of Nebraska, Omaha, Nebr.

[21] Appl. No.: 08/671,094

[22] Filed: Jun. 28, 1996

Related U.S. Application Data

[63] Continuation of application No. 08/311,380, Sep. 23, 1994, abandoned.

[51] Int. Cl.$^6$ .................................................... A61K 38/00
[52] U.S. Cl. ................................. 514/13; 514/12; 514/14; 514/15; 514/825; 514/886; 530/324; 530/325; 530/326; 530/327; 530/328
[58] Field of Search ................................. 514/12, 13, 14, 514/15, 825, 886; 530/324, 325, 326, 327, 328

[56] References Cited

U.S. PATENT DOCUMENTS 5,079,228  1/1992  Cohen et al. ............................. 514/12

FOREIGN PATENT DOCUMENTS

| 9006321 | 6/1990 | WIPO . | |
| 9204372 | 3/1992 | WIPO . | |
| 9205796 | 4/1992 | WIPO . | |
| 9309794 | 5/1993 | WIPO . | |
| WO93/11159 | 6/1993 | WIPO | C07K 13/00 |

OTHER PUBLICATIONS

Clark–Lewis, Ian, et al., Structure–Activity Relationships of Interleukin–8 Determined Using Chemically Synthesized Analogs, J of Bio Chem, vol. 266, No. 34, Dec. 5, 1991.

Moser, Bernhard, et al., Interleukin–8 Antagonists Generated by N–terminal Modification, J of Bio Chem, vol. 268, No. 10, Apr. 5, 1993.

Baldwin, Eric T., et al., Crystal structure of interleukin 8: Symbiosis of NMR and crystallography, Proc. Natl. Acad. Sci. USA, vol. 88, Jan. 1991.

Clark–Lewis, Ian, et al., Platelet factor 4 binds to interleukin 8 receptors and activates neutrophils when its N terminus is modified with Glu–Leu–Arg, Proc. Natl. Acad. Sci. USA vol. 90, Apr. 1993.

Clark–Lewis, Ian, et al., Structural Requirements for Interleukin–8 Function Identified by Design of Analogs and CXC Chemokine Hybrids, J. of Bio Chem, vol. 269, No. 23, Jun. 10, 1994.

Clore, G. Marius, et al., Determination of the Secondary Structure of Interleukin–8 by Nuclear Magnetic Resonance Spectroscopy, J. of Bio Chem, vol. 264, No. 32, Nov. 15, 1989.

*Primary Examiner*—Cecilia J. Tsang
*Assistant Examiner*—Jennifer Harle
*Attorney, Agent, or Firm*—Dann, Dorman, Herrell and Skillman

[57] ABSTRACT

Polypeptides derived from human interleukin-8 (IL-8) or other alpha chemokines which act as anti-inflammatory agents for the therapy of autoimmune disease, inflammatory conditions, and various chronic inflammatory diseases such as rheumatoid arthritis and psoriasis.

19 Claims, 6 Drawing Sheets

ANTI-INFLAMMATORY POLYPEPTIDE ANTAGONISTS OF HUMAN Il-8

This is a continuation of application Ser. No. 08/311,380, filed Sep. 23, 1994 now abandoned.

BACKGROUND OF THE INVENTION

The present invention relates to polypeptide antagonists of the human cytokine interleukin 8 or other alpha therapeutic chemokines and to the method of using these antagonists.

Interleukin 8 (IL-8) is a cytokine that promotes the recruitment and activation of neutrophil leulcocytes and represents one of several endogenous mediators of the acute inflammatory response. In the past it was variously termed neutrophil-activating factor, monocyte-derived neutrophil chemotactic factor, interleukin-8 (IL-8), and neutrophil-activating peptide-1. IL-8 has gained the widest acceptance and will be used herein.

The most abundant naturally occurring form of the IL-8 monomer is a 72-residue protein apparently derived by processing of a 99-residue precursor. Other proteins with related sequences, including neutrophil-activating peptide-2 1 ENS-78 and GROα (with melanoma growth stimulatory activity) are IL-8 homologues which have neutrophil-activating properties.

IL-8 is a member of the chemokine superfamily that is divided into two distinct function classes: alpha ($\alpha$) and beta ($\beta$). The members of each class share an organizing primary sequence motif. The $\alpha$ members are distinguished by a C-X-C motif with the first two cysteines in the motif separated by an intervening residue. C-X-C chemokines are potent chemoattractants and activators for neutrophils, and are represented by IL-8. The $\beta$ family chemokines have a C—C motif and are equally potent chemoattractants and activators of monocytes. It appears that the two sides of the chemokine family have clearly defined functions: the C-X-C subfamilies cannot activate monocytes while the C—C subfamily has no effect on neutrophils. Nonetheless these two families of chemokines have similar structures although fairly low sequence homology (30 to 35%). Proteins within the same family such as platelet factor four (PF-4) are structurally related to IL-8 (35% sequence identity) but in this example lack the N terminal ELR sequence (Glu-Leu-Arg) which has been shown by site directed mutagenesis to be critical for IL-8 activity and thus, PF-4 has an entirely different profile of activity. Indeed, when the ELR sequence is added to the N-terminus of PF-4 it has been found that the modified protein has potent neutrophil activation and chemoattractant properties (Clarlc-Lewis, I; Dewald, B.; Geiser, T.; Moser, B.; Baggiolini, M.: Platelet factor 4 binds to interleukin 8 receptors and activates neutrophils when its N terminus is modified with Glu-Leu-Arg. Biochemistry 90:3574–3577, 1993). However this may not be true for all of the chemokines since two of the proteins related to IL-8, γ interferon inducible protein (IP-10) and monocyte chemroattractant protein 1 (MCP-1) do not acquire neutrophil activating properties when the ELR structural determinants are added. Interestingly, when the E and the L of the ELk motif are removed from IL-8 the molecule acts as an antagonist for IL-8 (Moser, B.; Dewald, B.; Barella, L.; Schumacher, C.; Baggiolini, M.; Clark-Lewis, Lewis, I: Interleulin-8 antagonists generated by N-terminal modification. J Bio Chem 268:7125–7128, 1993).

In other studies by Clark-Lewis (Clark,Lewis, I., et al.: Structural requirements for interleukin-8 function identified by design of analogs and CXC chemokine hybrids. J Biol Chem 269:16075–16081, 1994) it was shown that conservative substitutions are accepted into the 10–22 region of IL-8 in contrast with the ELR motif (residues 4–6). They concluded that the disulfide bridges and the 30–35 turn provide a structural scaffold for the $NH_2$ terminal region which includes a primary receptor binding site (ELR motif) and secondary binding and conformational determinants as seen in residues 10 through 22. Other studies using mutants of IL-8 and melanoma growth stimulating activity (MGSA) and recombinant EL-8 α/β receptors stably expressed in human cells demonstrated that there was a second site on the molecule responsible for binding. It appears that the carboxy terminus distal to amino acid 50 is not important in high affinity binding to the α receptor although both the amino and carboxy termini appear to be important for binding to the β receptor (Schraufstatter, I. S., et al., Multiple sites on IL-8 responsible for binding to α and β IL-8 receptors. J Immunol 151:6418–6428, 1993). In summary, it appears that there are at least two and maybe three regions responsible for binding on IL-8. Further, the specific contact pharmacophore may vary depending upon whether or not the α or the β receptor is being examined.

Inflammation and autoimmune responses are initiated by leukocytes which migrate out of the microvasculature and into the extravascular space in response to chemoattractant molecules. These chemoattractants may be from the host and include cytolines, activated complement components or may be released from an invading organism (e.g., N-formylated peptides or MDP dipeptide). Once exposed to chemoattractants within the vasculature, the leukocytes become activated and capable of adhering to the endothelium providing the first step in the development of inflammation. Stimulated neutrophils adhere to the endothelium of the microvasculature in response to a gradient of chemoattractants which direct the cells into the extravascular space toward the source of the chemoattractant. (Anderson et al., J Clin Invest 74:536–551, 1984; Ley, K, et al., Blood 77:2553–2555, 1991; Paulson, J. C., Selectincarbohydrate-mediated adhesion of leukocytes, Adhesion: Its Role in Inflammatory Disease, W. H. Freeman, 1992; Lasky, L. A., The homing receptor (LECAM 1/L-selectin), Adhesion: Its role in inflammatory disease, W. H. Freeman, 1992.)

Bevilacqua et al., (J Clin Invest 76:2003–2011, 1985), demonstrated that cytokines and endotoxin stimulated the endothelium to become more adhesive for leukocytes. Subsequent observations (Buyon, J. P., et al., Clin Immunol Immunopathol 46:141–149, 1988; Abramson, S. B., et al., Hosp Pract 23:45–56, 1988; Clark-Lewis, I. et al., Biochemistry 90:3574–3577, 1993); have suggested that the endothelium has a critical role in the events leading to the development of the inflammatory lesion. This model of inflammation suggests that leukocytes are directed to an inflamed locus by stimulated endothelium. After stimulation with cytolkines or bacterial products, the endothelium arrests leukocytes as they traverse (roll along) the microvasculature near sites of inflammation. After being forced to stop in the microvasculature, the leukocytes are then activated to adhere more tightly to the endothelium and to migrate to the abluminal aspect of the vessel. The leukocyte, once it is out of the blood vessel is then capable of following a gradient of chemoattractants toward the exciting pathogen.

Vascular endothelium, activated by stimulants such as IL-1, IL-8, TNF, or LPS, appears to play a pivotal role in this process through the production of pro-inflammatory substances, including chemoattractants and cytokines such as chemokines.

The inflammatory properties of IL-8 were initially demonstrated from a purified natural product injected intradermally into rabbits to evaluate the proinflammatory properties, (Rampart, M. et al., Am J Path 135(1L):21–25, 1989). More recently neutralizing antibodies to human IL-8 were shown to have a protective effect in inflammatory lung injury in rats. This antibody blocked the glycogen-induced accumulation of neutrophils in rats and was protective against lung interdermal vascular injury induced by the disposition of IgG immune complexes. This latter model of injury has been shown to be E-selectin dependent. The protective effect of the neutralizing antibody correlated with reduced tissue accumulation of neutrophils as measured by myeloperoxidase content. Preliminary nonhuman primate studies have confirmed the activity of IL-8 on hematological parameters. IL-8 was administered by both bolus and continuous infusion to baboons. This resulted in a rapid, transient and severe granulocytopenia followed by granulocytosis that persisted as IL-8 levels remained detectable within the circulation. Histopathological examination revealed a mild to moderate neutrophil margination in the lung, liver and spleen which was of greater severity in animals receiving the continuous infusion of IL-8.

High levels of intravascular IL-8 have been reported in systemic conditions such as septic shock (Danner, R. L., et al., Clin Res 38:352A, 1990). These authors have speculated that intervascular IL-8 may impair leukocyte adhesion and thus protect organs from PMN mediated injury. The intravenous administration of IL-8 induced an immediate and transient neutropenia that was similar in kinetic profile to that described with other chemoattractants. This neutropenia was a result of pulmonary PMN sequestration and is consistent with the demonstration of abundant IL-8 receptor on PMNs. Following this transient neutropenia (approximately 30 minutes) cells recirculate with a normal half life. Shortly thereafter neutrophilia, a characterisic of IL-8, is observed. The neutrophilia likely reflects recruitment of mature PMNs to a marginal pool in the lung and other organs as well as immature PMNs from the marrow.

Endothelial cells can exert both proinflammatory and anti-inflammatory effects by virtue of the mediators they generate. Endothelial cells can be stimulated to generate IL-8, but unlike other mediators, IL-8 may be released from the endothelial cell. Alternatively, endothelial cell produced IL-8 is an important chemoattractant and activator of neutrophils. There is evidence that systemic IL-8 can bind to endothelial cells which could produce a local activation of the endothelium resulting in the ability of this altered endothelium to attract neutrophils that have come into contact with the (activated) endothelium. One working hypothesis is that IL-8 initially functions as a proinflammatory cytoline, whereas its continued generation and release from the endothelium ultimately causes a down regulation of neutrophils, with a curtailment in their further recruitment. Whether the cell associated IL-8 or released IL-8 provides the vital contribution to the outcome of the inflammatory response remains unresolved.

IL-8 receptors are "promiscuous" and respond with a calcium flux when bound by structurally related ligands with the following order of potency: IL-8>MGSA>NAP-2 which correlates with the effectiveness of these compounds when competing with the radio labeled IL-8 for binding to neutrophils C5a, a structurally related chemoattractant that is similar in size and charge to IL-8 and which has a receptor in the same family, does not activate the IL-8 receptor.

The in vitro effects of IL-8 on neutrophils are similar to those of other chemotactic antagonists such as C5a and fMet-Leu-Phe and include induction of a transient rise in cytosolic free calcium, the release of granules containing degradative enzymes such as elastase, the respiratory $H_2O_2$ burst, neutrophil shape change, and chemotaxis. IL-8 appears to bind to two or more receptor sites on neutrophils with a frequency of approximately 64,000/cell and a $K_d$ of 0.2 nM.

The three-dimensional structure of IL-8 is known by two-dimensional NMR and x-ray diffraction techniques. The IL-8 monomer has antiparallel β strands followed by a single overlying COOH-terminal α helix. Two disulfide bridges, between cysteines 7 and 34, and between cysteines 9 and 50 seem to stabilize the tertiary structure. Residues 1–6 and the loop residues 7–18 seem to have little defined secondary structure. En solution, IL-8 is a noncovalent homodimer which is stabilized primarily by interactions between the β strands of the two monomers.

Examination of the three-dimensional structure indicates that following the cysteine at position 50, the residues form a type 1β turn (at residues 51 to 55) followed by an amphipathic α helix (at residues 55 to 72) that transverses the β sheet. The hydrophobic face of the α helix interacts with and stabilizes the hydrophobic face of the β sheet. Some of the interactions are between the two subunits of the dimeric molecule.

As it is established that IL-8 is a key mediator of inflammatory diseases, it would be desirable to identify substances capable of blocking or interrupting the activity of IL-8 for use in anti-inflammatory compositions. Such compositions may prove to be advantageous over presently available NSAID's, steroid based anti-inflammatory drugs and cytotoxic drugs which often have severe side-effects with the continued usage that is required for chronic inflammatory diseases. It would also be desirable to identify IL-8 analogs having an increased inflammatory activity for medical research applications.

IL-8 has been previously produced through chemical synthesis (for example see: Clark-Lewis, et al., "Chemical Synthesis, Purification, and Characterization of Two Inflammatory Proteins; Neutrophil-Activating Peptide-1 (Interleuldn-8) and Neutrophil-Activating Peptide-2" (1991) Biochemistry 30: 3128–3135) and by recombinant DNA methods (for example see: Herbert, et al., "Scanning Mutagenesis of Interleukin-8 Identifies A Cluster of Residues Required for Receptor Binding" (1991) J. Biol. Chem. 286: 18989–18994). In addition, it is known that IL-8 exists in several forms that vary at the $NH_2$-terminus, which have been detected in preparations purified from natural sources. These variations correspond to the predominant 72-residue form (which is generally considered to be the prototype IL-8 molecule); a 77-residue form having 5 additional $NH_2$-terminus amino acids on each monomer; and, two shortened forms having residues 3-72 and 4-72 of the 72 amino acid form, respectively.

SUMMARY OF THE INVENTION

The present invention involves peptides which have antagonistic activity with IL-8 and comprise an amino acid sequence having the formula (SEQ. ID. NO. 11): Xaa Xaa Arg Cys Xaa Cys Xaa Xaa Xaa Xaa Xaa Xaa Xaa Xaa Xaa Xaa Xaa Xaa Xaa Xaa Xaa Xaa Xaa Xaa where in Xaa at the first position may be absent or may be any non-polar amino acid;

Xaa at the second position may be absent or may be any non-polar amino acid;

Xaa at the fifth position may be Gln, Met, Val, Leu, or Thr;

Xaa at the seventh position may be Ile, Leu, or Val;

Xaa at the eighth position may be Lys, Gln, or Ser;

Xaa at the ninth position may be Thr, or Ile;

Xaa at the tenth position may be Tyr, Thr, Leu, Met, Val, or His;

Xaa at the eleventh position may be Ser, Gln, Ala, or Thr,

Xaa at the twelfth position may be Lys, Arg, Gly, Val, or His;

Xaa at the thirteenth position may be Phe, Gly, Ile, His, Val, or Pro;

Xaa at the fourteenth position may be absent or is Ile, Val, His, Leu, or Phe;

Xaa at the fifteenth position may be absent or is His, Pro, Leu, Phe, Arg or Lys;

Xaa at the sixteenth position may be absent or is Pro, Lys, Phe, or Leu;

Xaa at the seventeenth position may be absent or is Lys, Arg, or His;

Xaa at the eighteenth position may be absent or is any amino acid;

Xaa at the nineteenth position may be absent or is any amino acid;

Xaa at twentieth position may be absent or is any amino acid;

Xaa at the twenty-first position may be absent or is any amino acid;

Xaa at the twenty-second position may be absent or is any amino acid;

Xaa at the twenty-third position may be absent or is any amino acid;

Xaa at the twenty-fourth position may be absent or is any amino acid;

Xaa at the twenty-fifth position may be absent or is any amino acid;

Xaa at the twenty-sixth position may be absent or is any amino acid.

More particularly, in the preferred embodiment the present invention comprises an amino acid sequence substantially equivalent to Arg-Cys-Gln-Cys-Ile-Lys-Thr-Tyr-Ser-Pro-Phe-His-Pro-Lys as well as similar analogs having either one or two additional N-terminal amino acids such as alanine. Another embodiment of the present invention comprises an amino acid sequence substantially equivalent to polypeptides acting as anti-inflammatory agents for the therapy of autoimmune disease, and various acute or chronic inflammatory states such as rheumatoid arthritis and psoriasis.

In embodiments of the invention, the low molecular weight polypeptide analog for IL-8 or other alpha chemokines is modified selectively to provide antagonists of IL-8. In one particular embodiment, antagonists that compete strongly with IL-8 for neutrophil binding without signal transduction are obtained by deleting Glu-Leu (amino acid residues 4 and 5). In another particular embodiment, antagonists that compete with IL-8 yet still retain antagonist properties are obtained by replacing at least residue Glu and Leu with non-polar amino acids, such as Ala, Val or Leu or other amino acids.

Several low molecular weight peptide analogs of IL-8 were investigated and it has been determined unexpectedly that truncation of the form of IL-8, particularly in the N terminal region thereof, yields IL-8 low molecular weight peptide analogs having therapeutically useful properties. More particularly, the antagonist IL-8 low molecular weight peptide analog of the present invention comprises an amino acid sequence with biological activity that substantially competes for IL-8 binding and is based on the IL-8 sequence beginning at residue 6 and continuing through residue 19, wherein at least on the N-terminal residues found to be critical for neutrophil binding and stimulation, i.e., Arg-6 is contained at the N-terminal region.

In other embodiments of the invention, the IL-8 moiety is truncated from residue 20 to the C-terminus as well as N-terminal residues 1 to 5. This embodiment provides pharmaceutical compositions of the aforementioned analogs comprising the analog and a suitable carrier therefore. Also provided are methods of the use of the aforementioned analogs.

IL-8 analogs having the form including an additional one or two polar residues at the amino terminus of the 14 residue peptide so as to provide the 4 or 5–19 forms are also useful as IL-8 antagonists. In addition, significant biological activity is associated with a low molecular weight peptide analog from residue 6–16 resulting in an 11 amino acid peptide with antagonist activity for IL-8.

Accordingly, this invention provides a biologically active human interlekin-8 antagonist which is a low molecular weight peptide analog having an amino acid sequence substantially equivalent to the IL-8; 6 through 19 or 6 through 16 sequence beginning at residue 6 and continuing to residue 16 or 19. Further, equal or greater activity is associated with the addition of Ala, Val, Leu or other amino acid at residue 4 and 5.

This invention also provides methods of use of these antagonistic analogs. In addition, this invention also provides methods of use of additional low molecular weight peptide analog with conservative substitutions and/or additions in the sequence.

In contrast to the claimed invention in PCT/CA92/00528 which describes a 77 amino acid antagonist to IL-8, the embodiment of the present invention is a low molecular weight peptide antagonist which is 11 to 14 amino acids in length. This allows the more rapid and extensive tissue distribution of the drug on administration as compared to a 70 amino acid therapeutic. Further, this invention substantially increases the purity of the product through reduced errors inherent to the manufacture of a large protein. In addition this invention has a significant reduction in the cost of goods as compared to the invention in the aforementioned patent versus the present invention. Based on the homogeneity of the alpha chemokines, both sequence and three dimensional, antagonists for both known and additional alpha chemokines can be derived based on the present invention. The present claims include information on the reduction to practice of an invention specific for the IL-8 ligand and receptor.

BRIEF DESCRIPTIONS OF THE DRAWINGS

FIG. 1: A graph showing the effects of arachidonic acid induced ear inflammation in mice as a function of administration of Analog 1.

FIG. 2: A graph showing the effects of arachidonic acid induced ear inflammation in mice as a function of administration of Analog 1.

FIG. 3: A composite of FIGS. 1 and 2 showing the effects of arachidonic acid induced ear inflammation in mice as a function of administration of Analog 1.

FIG. 4: FACS analysis profile showing the increase in calcium as a result of stimulation of neutrophils with native IL-8. FIG. 4A, unstimulated; FIG. 4B. stimulated with IL-8.

FIG. 5: FACS analysis profile showing the treatment of neutrophils with excipients. FIG. 5A, untreated; FIG. 5B, PBS treated.

FIG. 6: FACS analysis profile showing the inhibition of calcium release from neutrophils treated with native IL-8 and Analog 1. FIG. 6A: untreated; FIG. 6B, IL-8 and Analog 1 treated.

DETAILED DESCRIPTION OF THE INVENTION

Figure 1:
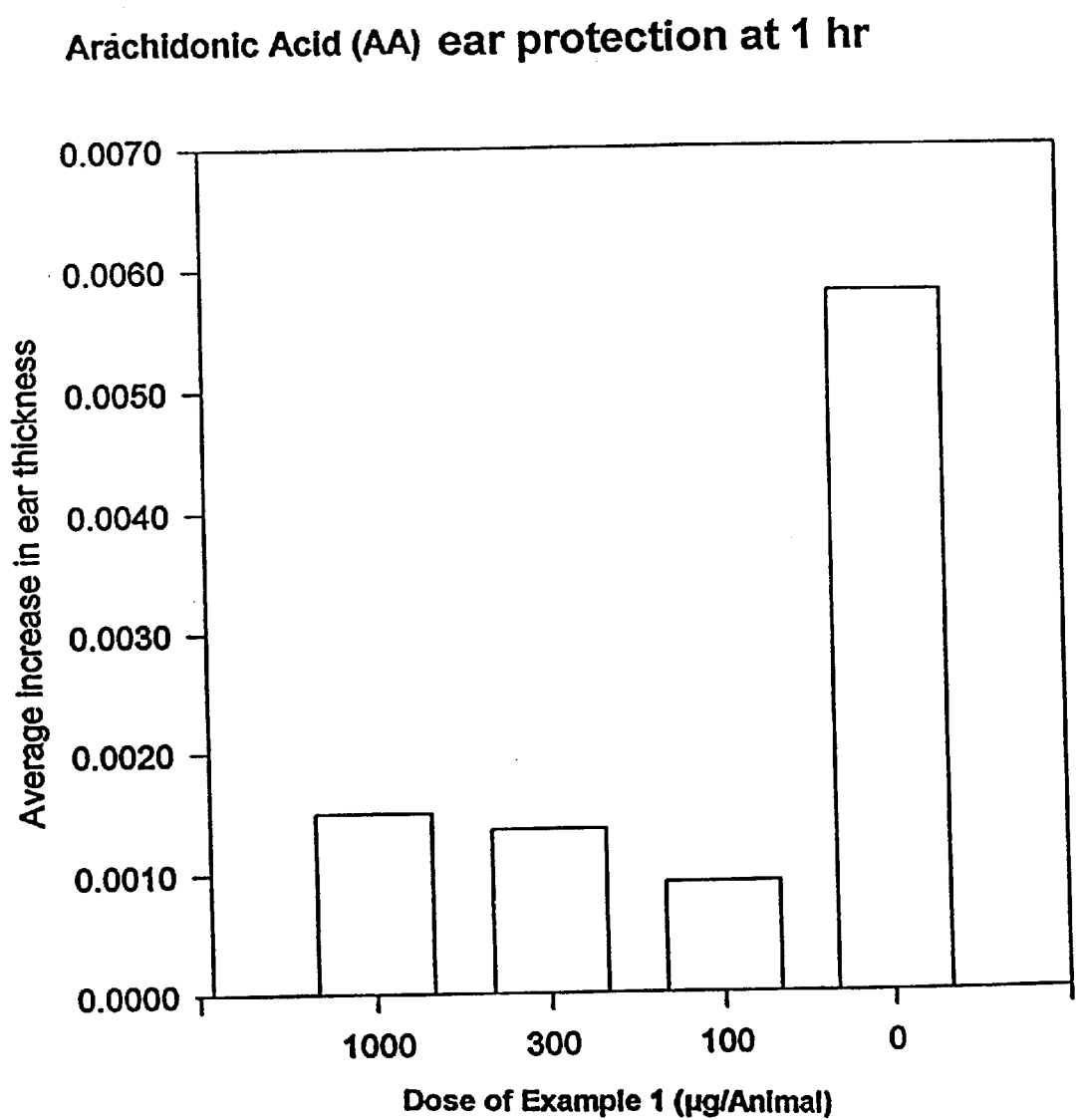

In order to provide an understanding of several of the terms used in the specification and claims, the following definitions are provided:

Biological activity

The term biological activity is a function or set of functions performed by a molecule in a biological context (i.e., in an organism or an in vitro surrogate or facsimile model). For IL-8 or other alpha chemokine biological activity is characterized by its chemotactic activity (preferably PMNs but may also include T lymphocytes and/or monocytes/ macrophages). It may also include second messenger and/or increases in elastase activity by PMNs.

A low molecular weight peptide analog

This identifies a natural or mutant (mutated) analog of a protein, comprising a linear or discontinuous series of fragments of that protein in which one or more amino acids have been replaced with other amino acids and which has altered, enhanced or diminished biological activity when compared with other amino acids and which has altered, enhanced or diminished biological activity when compared with the parent or non-mutated protein.

Substantially equivalent biological activity

Is that profile of activity which defines IL-8 or other alpha chemokine. In in vitro surrogate models this may include chemotaxsis of PMNs, T lymphocytes or monocytes; Ca signal transduction; or increases in elastase activity. In vivo this would be defined as the chemotaxsis of PMNs to a localized site or to the peripheral blood for example the peritoneum following ip injection.

TABLE 1

The amino acids are identified in the present application according to the three-letter or one-letter abbreviations in the following Table 1:

| Amino Acid | 3-letter Abbreviation | 1-letter Abbreviation |
| --- | --- | --- |
| L-Alanine | Ala | A |
| L-Arginine | Arg | R |
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Norleucine | NorLeu | J |
| L-Ornithine | Orn | O |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| "Asx" means Asp or Asn | | |
| "Glx" means Glu or Gln | | |
| L-Lysine | Lys | K |

TABLE 2

Preferred embodiments of the peptides of the present invention are presented in Table 2 which follows:

Analog 1 (SEQ. ID. NO. 1):
Derived from Alpha Chemoline—IL-8 (also called NAP-1)
Arg-Cys-Gln-Cys-Ile-Lys-Thr-Tyr-Ser-Lys-Pro-Phe-His-Pro-Lys Analog 2 (SEQ. ID. NO. 2):
Derived from Alpha Chemokine—GRO (also called MGSA)
Arg-Cys-Gln-Cys-Leu-Gln-Thr-Leu-Gln-Gly-Ile-His-Pro-Lys Analog 3 (SEQ. ID. NO. 3):
Derived from Alpha Chemokine—GRO-β (also called MIP-2α)
Arg-Cys-Gln-Cys-Leu-Gln-Thr-Leu-Gln-Gly-His-Leu-Lys Analog 4 (SEQ. ID. NO. 4):
Derived from Alpha Chemokine—GRO
Arg-Cys-Gln-Cys-Leu-Gln-Thr-Met-Thr-Gly-Val-His-Leu-Lys Analog 5 (SEQ. ID. NO. 5):
Derived from Alpha Chemokine—GRO (also called MEP-2β)
Arg-Cys-Gln-Cys-Leu-Gln-Thr-Leu-Gln-Gly-His-Leu-Lys Analog 6 (SEQ. ID. NO. 6):
Derived from Alpha Chemokine-B thromboglobulin (also called NAP-2)
Arg-Cys-Met-Cys-Ile-Lys-Thr-Thr-Ser-Gly-Ile-His-Pro-Lys Analog 7 (SEQ. ID. NO. 7):
Derived from Alpha Chemokine—9E3
Arg-Cys-Gln-Cys-Ile-Ser-Thr-His-Ser-Lys-Phe-le-His-Pro-Lys Analog 8 (SEQ. ID. NO. 8):
Derived from Alpha Chemokine—31C
Arg-Cys-Gln-Cys-Ile-Lys-Thr-Tyr-Ser-Lys-Pro-Phe-His-Pro-His Analog 9 (SEQ. ID. NO. 9):
Derived from Alpha Chemokine—CNC
Arg-Cys-Gln-Cys-Leu-Gln-Thr-Val-Ala-Gly-Ile-His-Phe-Lys Analog 10 (SEQ. ID. NO. 10):
Derived from Alpha Chemokine—ENA-78
Arg-Cys-Val-Cys-Leu-Gln-Thr-Thr-Gln-Val-Gly-His-Pro-Lys The present invention includes analogs that are essentially equivalent to any analog of the invention specified in Table 2. An analog is essentially equivalent to one specified above if it has one or more of the biological activities characteristic of human IL-8 or other alpha chemokine, has essentially the same number of amino acids as the specified analog (with one amino acid addition or deletion) and, in comparison with the sequence of the specified analog, has at most five amino acid substitutions, all of which would be considered neutral in the art (i.e., acidic for acidic, basic for basic, uncharged polar for uncharged polar, hydrophobic for hydrophobic, and the like).

The acidic amino acids are Asp, Glu and gammacarboxy-glutamic acid. The basic amino acids are Arg, Lys, His and Orn. The hydrophobic amino acids are Ala, Ile, Leu, Met, Nor, Phe, Trp, Tyr, Val, t-butylglycine, norvaline, cyclohexylalanine, t-butylalanine, amino-4phenybutyric acid, beta-2-thienylala nine, p-bromophenylalanine, p-chlorophernylalanine, p-iodophenylalanine, p-nitrophenylalanine, 3.5-diiodotyrosine, phenylglycine, and napthylalanine. Uncharged polar amino acids are Asn, Gln, Ser, and Thr. Gly can be substituted for an uncharged polar or a hydrophobic amino acid, but substitutions with Pro are avoided because helical structures may be destabilized by such a significant effect on secondary structure of inserting a Pro in place of another amino acid.

Substitutions with Cys are specified and may include substitution with α-aminobutyric acid (Aba). This non-natural amino acid is suggested to cause a super-imposition with cysteine. Its ethyl side chain is closer to being isoteric than any of the naturally occurring non-polar amino acids. In addition, it is specified that Cys can be substituted with homocysteine or diaminosuberic acid replacing the cysteines thereby retaining charge and size conformation but in the absence of homodimerization.

The chiral amino acids of the IL-8 analogs of the present invention have the L configuration.

Analog 1 was designed as a structural mimic of IL-8 from amino acid residues 6 to 19. Analog 1 contains overall homology with the amino acid sequence of human IL-8.

Analog II was designated as a structural mimic of human IL-8 from amino acid residues 6 to 16. Analog 2 has been C-terminally truncated compared to analog 1, with slight loss of activity, compared to analog 1.

The analogs of the present invention can be made by exclusively solid phase techniques, by partial solid-phase techniques, by fragment condensation, by classical solution coupling, or, as long as the analog consists of only amino acids among the twenty naturally occurring amino acids corresponding to codons of the genetic code, by employing recombinant DNA techniques with bacteria, such as *E.coli* or *B.subtilis;* yeast, such as *S.cerevisiae* or *P.pastoris;* or insect or mammalian cells.

Methods of malting a polypeptide of known sequence by recombinant DNA techniques are well-known in the art. See, e.g., U.S. Pat. No. 4,689,318, which is incorporated herein by reference.

Methods for chemical synthesis of polypeptides are also well-known in the art and, in this regard, reference is made, by way of illustration, to the following literature: Yamashino and Li, J Am Chem Soc 100:5174–5178, 1978; Stewart and Young, Solid Phase Peptide Synthesis (W H Freeman and Co. 1969); Brown et al., J C S Perlin I, 1983, 1161–1167; M. Bodanszky et al., Bioorg Chem 2:354–362, 1973; U.S. Pat. Nos. 4,689,318; 4,632,211; 4,237,046; 4,105,603; 3,842,067; and 3,862,925, all of which are incorporated herein by reference.

Preferred, automated, step-wise solid-phase methods for synthesis of peptides of the invention are provided in the examples below.

The biological activity of an analog of the invention is determined by blocking with the analog an activity with naturally occurring IL-8.

The biological act of an analog of the invention for an alpha chemokine is determined by bloking with the analog a biological activity by the specific parent alpha chemokine.

Data for analogs of the invention from various assays are presented in the examples below.

The analogs of the invention are employed therapeutically, under the guidance of a physician for the treatment of anti-inflammatory and autoimmune disease.

The preferred use of the analogs of the invention is for, but not limited to, the treatment of chronic and acute inflammatory and auto-immune diseases such as SLE, GVHD, RA, IBD, asthma and Psoriasis.

The dose and dosage regiment of an analog according to the invention that is suitable for administration to a particular patient can be determined by a physician considering the patient's age, sex, weight, general medical condition, and the specific condition and severity thereof for which the analog is being administered; the route of administration of the analog; the pharmaceutical carrier with which the analog may be combined; and the analog's biological activity, relative to that of naturally occurring human IL-8, in the above-described assays.

Generally, intravenous subcutaneous or transmuscular injection of 1–500 μMol of analog/kg body weight, by bolus injection, by infusion over a period of about 5 minutes to about 60 minutes, or by continuous infusion is sufficient for therapeutic efficacy. Aerosol inhalation of 0.1 or 2 mg of analog/kg body weight is also sufficient for efficacy.

Intravenous, subcutaneous or intramuscular administration, by bolus injection or continuous infusion, is preferred for use of the analogs of the invention in treatment of autoimmune or inflammatory disease.

The analogs of the invention, or a pharmaceutically acceptable salt thereof, can be combined, over a wide concentration range (e.g., 0.001 to 11.0 wt %) with any standard pharmaceutical carrier (e.g., physiological saline, THAM solution, or the like) to facilitate administration by any of various routes including intravenous, subcutaneous, intramuscular, oral, or intranasal, including by inhalation.

Pharmaceutically acceptable acid addition salts of the analogs of the invention can be prepared with any of a variety of inorganic or organic acids, such as for example, sulfuric, phosphoric, hydrochloric, hydrobromic, nitric, citric, succinic, acetic, benzoic and ascorbic. The analogs can, for example, be advantageously converted to the acetate salt by dissolution in an aqueous acetic acid solution (e.g., 10% solution) followed by lyophilization.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form in which case solid Pharmaceutical carriers are obviously employed. If desired, tablets may be sugar-coated or enteric-coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain dosage unit, e.g., tablet, capsule, powder, infection, teaspoonful and the like, from about 0.001 to about 10 mg/kg, and preferably from about 0.01 to about 0.1 mg/kg of the active ingredient.

The following examples are provided to further illustrate the present invention and are not intended to limit the invention beyond the limitations set forth in the appended claims.

EXAMPLE 1

Peptides were synthesized using solid-phase methodology, generally described by Merrifield (J Amer Chem Soc 85:2149, 1963) (see also Stewart and Young, supra) with various modifications described herein, carried out on a Applied Biosystems 431A automated peptide synthesizer (Applied Biosystems, Foster City, Calif., USA).

Sequential assembly of a peptide analog is conducted from the carboxy-terminus, bonded to a solid-phase resin, to the amino terminus; the addition of amino acids to a peptide chain is automated after the attachment of the carboxy-terminal amino acid to the resin.

For peptides that will have a carboxyl group at the carboxy-terminus, p-chloromethyl-derivatized polystyrene supports are employed, and the carboxy-terminal amino acid is esterified to the support via reaction with KF as described by Horiki et al., Chem Lett 1978, 165–168. Analogs with a C-terminal proline or a penultimate C-terminal proline may be synthesized using a 2-chlorotrityl chloride derivatized resin. Attachment of FMOC amino acids to the resin can be quantitated by spectrophotometric determination at 266 nm following treatment of a weighed sample with 50% piperidine in DMF. Substitution levels for automated syntheses are preferably between 0.2 and 0.6 mmol amino acid per g resin. A typical FMOC synthesis is performed on a scale of 0.1–0.25 mmol and thus is initiated with 0.15–1.25 g amino acid-derivatized resin. Steps in the syntheses of the IL-8 analogs employed the following Protocol I(a):

| Step | Reagent | Mix Time (min) | # of Times |
|---|---|---|---|
| 1 | 20% piperidine in NMP | 16.4 | 2 |
| 2 | 0.45 M HBTU/HOBT in DMF/in NMP | 7.6 | 1 |
| 3 | NMP | 4.6 | 1 |
| 4 | 2.0 M DIEA in NMP | 2.2 | 1 |
| 5 | NMP | 22.2 | 1 |
| 6 | 0.5 M acetic anhydride/0.125 M DIEA/0.015 M HOBT/in NMP | 6.4 | 1 |
| 7 | NMP | 4.6 | 1 |
| 8 | Stop or return to step 1 for next coupling | | |

NMP = N-Methylpyrrolidone
HBTU = 2-(1H-benzotriazol-1-yl)-1,1,3,3-tetramethyluronium hexafluorophosphate
HOBT = 1-Hydroxybenzotriazole
DMF = Dimethylformamide
DIEA = Diisopropylethylamine All chemicals were reagent or peptide synthesis grade and were used as purchased. DIEA and NMP were from Fisher Scientific, Fair Lawn, N.J., USA. Piperidine, HOBT and HBTU were from Advanced ChemTech, Louisville, Ky., USA. DMF was from E. Merck, Gibbstown, N.J., USA,. Acetic anhydride was from FLUKA, Buchs, Switzerland. The coupling of amino acids was carried out for 45 minutes with a four-fold excess of the activated esters of the FMOC amino acids with respect to the available amine sites on the resin.

The 9-Fluorenyl methoxycarbonyl (FMOC) group was used for protection of the alpha amine group of all amino acids employed in the syntheses; however, other protecting groups known in the art for alpha amines can be employed successfully. Side-chain functionalities were protected as follows: Arg with 4-Phenylazobenzyloxycarbonyl; Cys, Gln, and His with trityl; Glu, Ser, and Thr with benzyl; Lys with tertiary butyloxycarbonyl; and Tyr with tertiary butyl.

Resins employed in the syntheses were purchased with the C-terminal residue already attached to derivatized polystyrene- 1% divinyl-benzene (200–400 mesh), either by 4-hydroxymethylphenoxyacetic acid or 2-chlorotrityl chloride.

After assembly of the completed analog, the amino-terminal FMOC group is removed using step 1 of the above protocol and then the resin is washed with methylene chloride and dried. The analogs are then deprotected and removed from the resin support by treatment with TFA for 2 hours at 25 degree(s) C. The peptide is precipitated with cold diethyl ether, the liquid phase is filtered away and the peptide is extracted with 10% acetic acid in water and lyophilized.

The resulting crude preparations were purified by preparative high performance liquid chromatography (HPLC) on a Waters C-18 column (40×200 mm) (Millipore Corp, Miliford, Mass., USA) and analyzed by analytical HPLC. Preparative HPLC separations were performed with the Waters column on a Waters Delta Prep 4000 System (Millipore Corp, Millfrd, Mass., USA) at a flow rate of 75 ml/min. Samples were introduced in 0.1% TFA (running buffer) and after a 5 minute lag to ensure complete loading, eluted from the column with a 1%/minute acetonitrile gradient with an elution time of 24–26 minutes. Peptide fractions were monitored by UV absorbance at 220 nm. In all cases, fractions were manually collected at peak detection. The purified fractions were analyzed on an analytical HPLC System, Waters 712 WISP, using a Waters C-18 column (8×100 mm) using 0.1% TFA and an acetonitrile gradient. Other HPLC buffer systems which may be employed in the analytical HPLC include triethylamine phosphate (TEAP), pH 2.5–3.0, TEAP, pH 6.5, and a mixture of 0.1% phosphoric acid, 0.1M sodium perchlorate, pH 2.5 with an acetonitrile gradient. Although the TPA buffer system does not resolve microheterogeneous contaminants as well as other systems, recovery is generally 50–90% higher. A portion of a fraction from the preparative HPLC which appeared homogenous by analytical HPLC was removed, lyophilized and hydrolyzed for amino acid analysis. These portions with the proper amino acid compositions and proper mass, determined by matrix assisted laser desorption ionization—time of flight (MALDI-TOF) mass spectometry, were treated to replace the TFA with acetic acid and were then subjected to bioassay.

For amino acid analysis, a sample of analog was hydrolyzed in 6N HCI containing 1% phenol for 70 minutes at 110 degrees C. Analyses were performed by a procedure which is a modification of the method of Cohen and Michaud (Anal Biochem 211:279–287, 1993) employing the AccQ Tag reagent (Waters, Millford, Mass., USA).

(a) SYNTHESIS OF THE IL-8

The synthesis of Analog 1, IL-8, was initiated by using 581 mg of an H-LYS(BOC) 2-chlorotrityl resin (substitution level=0.43 mmol/g), purchased from AnaSpec, Inc., (San Jose, Calif., USA). The synthesis was carried out automatically by the ABI 431A Peptide Synthesizer. The amount of components is summarized in the following Table 1 (b):

| CYCLE | Grams/protected amino acid |
|---|---|
| 1 | .337 P |
| 2 | .620 H |
| 3 | .387 F |
| 4 | .337 P |
| 5 | .469 K |
| 6 | .327 S |
| 7 | .494 Y |
| 8 | .341 T |
| 9 | .469 K |
| 10 | .353 I |

-continued

| CYCLE | Grams/protected amino acid |
|---|---|
| 11 | .586 C |
| 12 | .612 Q |
| 13 | .586 C |
| 14 | .397 R |

Upon completion of the synthesis, 0.8 g of peptide-resin was obtained. This was added to 10 ml of TFA in a 100 ml round bottom flask with 500 µl of $H_2O$ 500 µl thioanisole, 250 µl ethanedithiol and 750 mg phenol and stirred at 25 degree(s) C for 2 hours. The reaction was terminated by the addition of 100 ml cold diethyl ether to precipitate the peptide. The solution was filtered and the peptide was extracted with 100 ml 10% acetic acid in water, frozen, and lyophilized. A small portion was dissolved in 225 µl of 0.1% TFA and injected onto the analytical HPLC using the previously described conditions to determine elution characteristics for the preparative scale purification. The remainder of the crude peptide was loaded onto the preparative system and eluted under the above conditions. A 0–40% acetonitrile gradient over 40 minutes was used to elute the peptide components. An aliquot of homogeneous fractions from preparative HPLC was removed, and then hydrolyzed for amino acid analysis. Amino acid analysis results: Ser (1)0.96, Glx (1)0.96, His (1)1.04, Thr (1)0.94, Arg (1)1.08, Pro (2)1.82, Cys (2)1.86, Tyr (1)1.07, Lys (3)2.94, Ile (1)1.13, Phe(1)1.14. The MALDI-TOF mass spectrum showed the proper mass peak and only peptide-matrix peaks. Amino acid analysis of a weighed sample Analog 1 showed the powder to be 88.1% peptide by mass.

EXAMPLE II

In vivo Bio Assay of IL-8 Analogs

A stock solution of 5 mgml of example 1 was prepared in D-PBS. The Analog 1 consists of 88.1% active peptide and the calculations were adjusted to compensate for the activity of the Analog 1. Serial dilutions were then made resulting in solutions of appropriate doses of Analog 1 in 0.2 ml. The animals were injected ip with 0.2 ml of the appropriate solution 1 hour prior to arachidonic acid application.

The study consisted of various dosage groups as well as excipient groups.

The animals used for the study were C57BL/6 female mice, which were obtained from Jackson Laboratories (age 8 weeks and weight 15–18 g). The mice were housed in conventional cages, fed pelleted food and given water ad libitum.

The arachidonic acid (Sigma Lot #42H7817) was dissolved in methyl alcohol resulting in a final concentration of 2 mg/20 µl. At time zero, 10 µl of arachidonic acid was applied to each side of the test ear using a pipettor. Each mouse received a total of 2 mg and a total volume of 20 µl. One hour post challenge, the test and control ears were measured for thickness using a Mitutoyo No. 7300 gauge caliper. The thickness was recorded in units of 0.001 inches. To determine the total edema, the measurement of the control ear was subtracted from the test ear measurement (arachidonic acid ear).

EXAMPLE III

In Vitro Bic Assay of IL-8 Analogs

Cell Preparation

Polymorphonuclear leukocytes ($\geq 95\%$ neutrophils, PMNs) were isolated from heparinized (10 µ/ml) blood collected from healthy volunteers. Erythrocytes were removed by 6% dextran sedimentation for 30 minutes at room temperature, and then the supernatant was subjected to Ficoll (Ficoll-Papque, Pharmacia LKB, Uppsala, Sweden) density gradient centrifugation. PMNs were obtained from the pellet. Contaminated erythrocytes were eliminated by one cycle of hypotonic lysis. After an additional washing step the cells were counted and adjusted to a final concentration of $5 \times 10^6$/ml in RPMI 1640 (Gibco, Grand Island, N.Y.).

Fluo-3 Loading

The loading procedure with Fluo-3 (Molecular Probes, Eugene, Oreg.) was carried out with PMNs suspended at a density of $5 \times 10^6$/ml in fresh RPMI 1640 containing 2.0 µM Fluo-3 AM (prediluted in dimethyl sulfoxide; Sigma Chemicals) in polypropylene tubes (Falcon 2063, Becton Dickinson). We incubated the PMNs for 25 minutes at 37 degrees C in a 5% $CO_2$ incubator. During the incubation period the PMNs were gently agitated twice. To remove extracellular Fluo-3 AM, cells were washed twice with RPMI 1640 and with $Ca_{2+}$ and $Mg_{2+}$-free phosphate-buffered soline (PBS) containing 100 mM KC1 and 5 mM HEPES buffer at pH 7.05. Finally, the cells were adjusted to a density of $5 \times 10^5$/100 µl in the PBS buffer and suspended in 5×35 mm tubes. The samples were kept in the dark at room temperature until use.

Measurement of $[Ca^{2+}]$ in Flow Cytometry

Before addition of the stimuli the fluorescence channel of the FACScan Plus (Becton Dickinson) was adjusted to find the basal fluorescence level of loaded but unstimulated PMNs. The samples were excited by an argon laser at 488 nm and emission was measured at 525 nm (green fluorescence, channel FL1). The temperature has no effect on the appearance of neutrophil subpopulations with different $[Ca^{2+}]$ mobilizations. However, the experiments were carried out at room temperature (22 degrees C.). PMNs were then stimulated at different concentrations with IL-8/NAP-1 with or without the addition of the antagonist. The events were acquired before and 5 s after addition of the stimuli, and acquisition was continued over 80 s. For each acquisition 2500–3000 events were collected in 6 s interrupted for a time interval of 8 s or less using the FACScan software (Becton Dicidnson). The fluorescence of Fluo-3-loaded cells was measured in arbitrary fluorescence units of mean channel fluorescence (channel FL1). To control the influence of the medium, PBS (supplemented as described above) was added instead of stimuli. A continuous measurement of unstimulated PMNs was also carried out. Both procedures did not result in an increase in arbitrary fluorescence units.

ANALOG IV

In vivo bioactivity of Example I

The effect of Analog 1, which is on IL-8 low molecular weight peptide analog residue 6-19 on arachidonic acid induced ear inflammation was evaluated in vivo, according to the methods described in Example II. In this model, the application of arachidonic acid to the pinna of mice induces an immediate PMN-associated erythema and edema which may be measured by change in thickness. As shown in FIGS.

Figure 2:
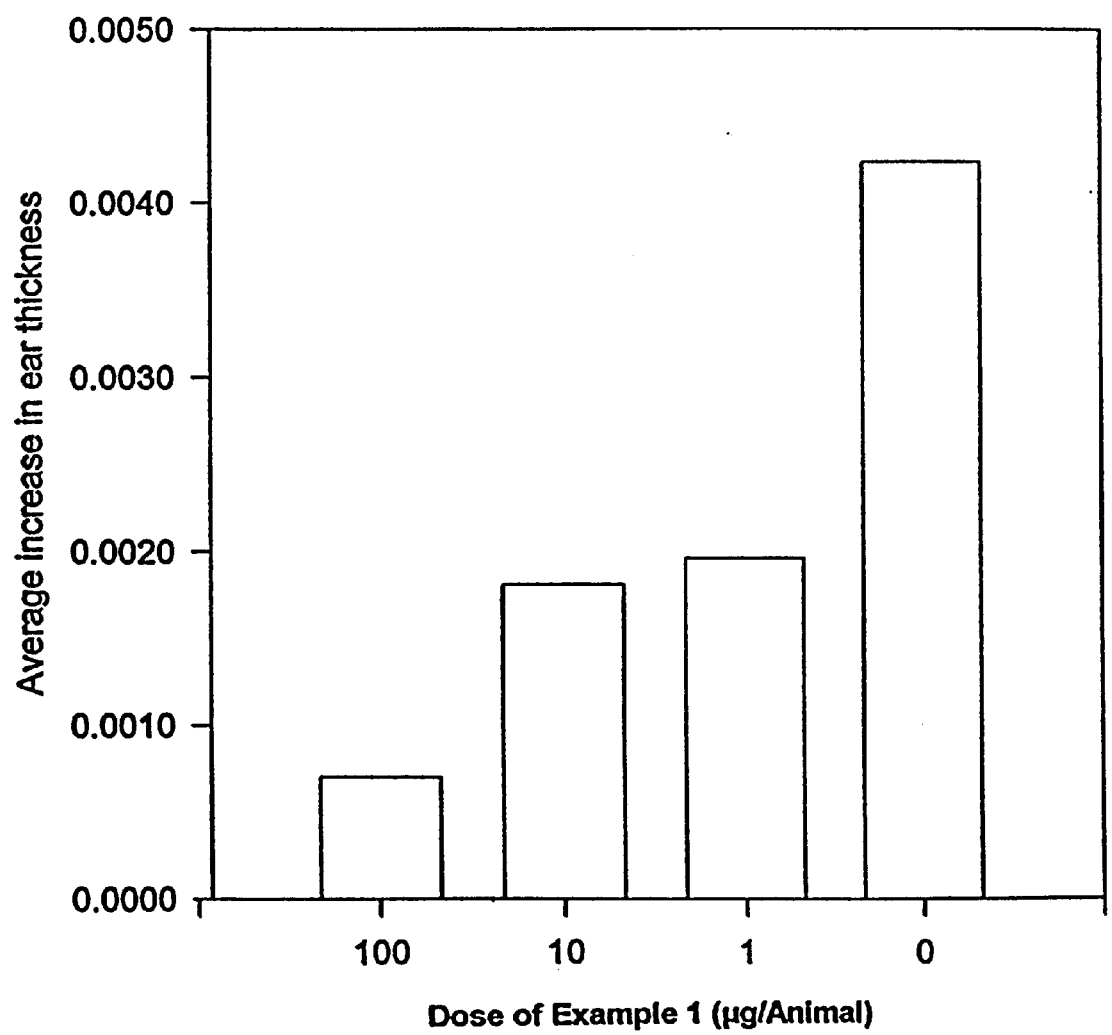
Figure 3:
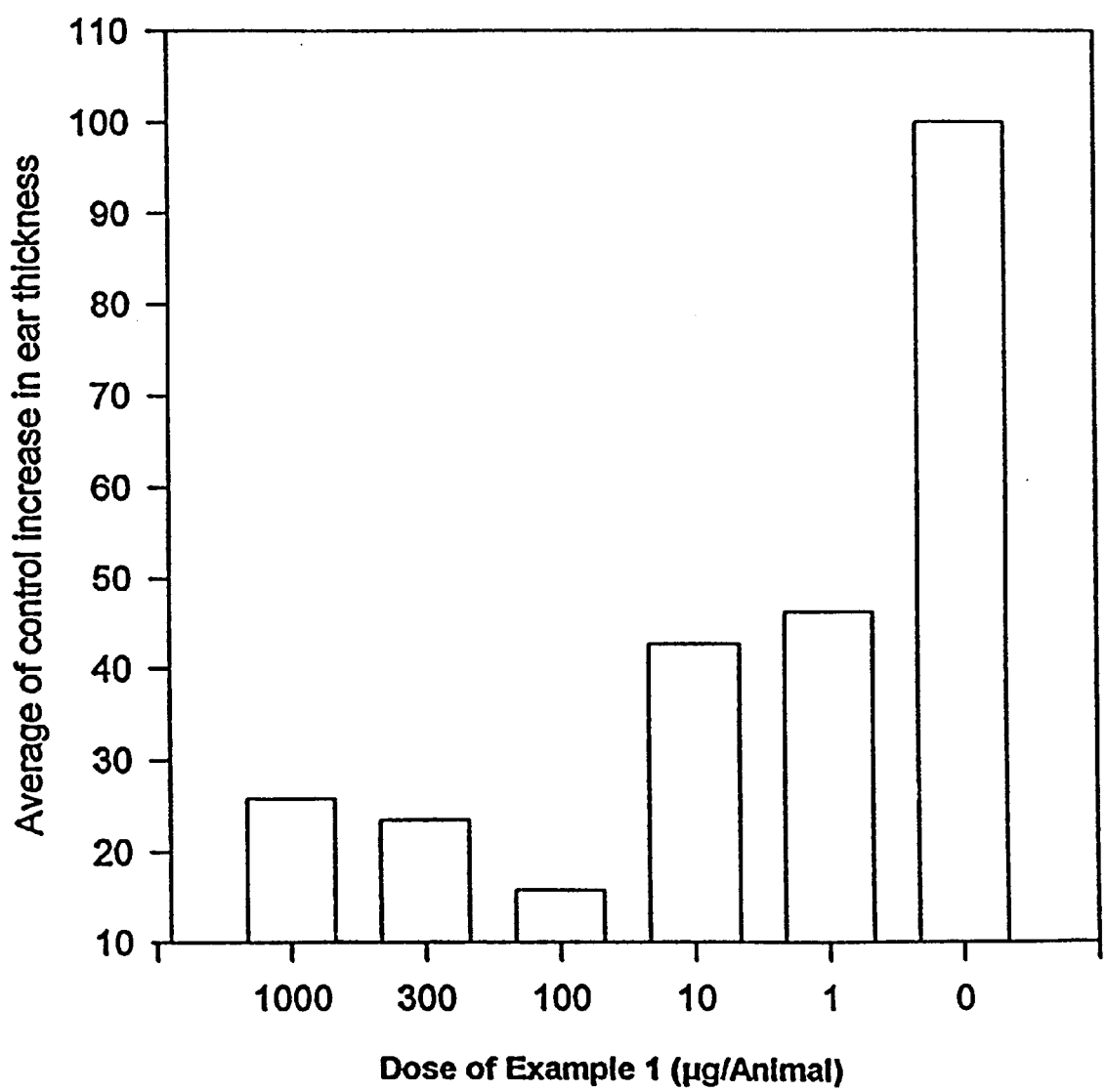

1 and 2 the administration of this low molecular weight peptide analog blocked edema with an approximate EC-50 of 1 μg/animal. In other recent studies in our laboratory similar suppression of arachidonic acid induced inflammation in the mouse pinna was observed with 100 mg/kg phenidone (NSAID). In addition, FIG. 3 represents all the data of FIG. 1 and 2 and is reported as the average of control increase in ear thickness These results are substantially the same as that reported in Internation Application No. PCT/CA92/00528. In this study, N-terminally truncated natural IL-8 (70 amino acids) was shown to inhibit inflammation using the rabbit plasma exudate dermal assay reported by Beaubien et al. (Biochem J. 1990, 271:801). In this model, anti-inflammatory activity is monitored by a reduced edema formation and neutrophil accumulation in rabbit skin. In contrast to the studies shown in patent PCT/CA92/00528, Analog 1 is a 14 amino acid antagonist. The compound described in the aforementioned patent, is a full length antagonist and comprises 70 amino acids requiring extensive synthesis and/or recombinant production substantially increasing both the cost of good and the probability of synthetic errors during the process.

ANALOG V

In vitro activity of Example I

Figure 4A:
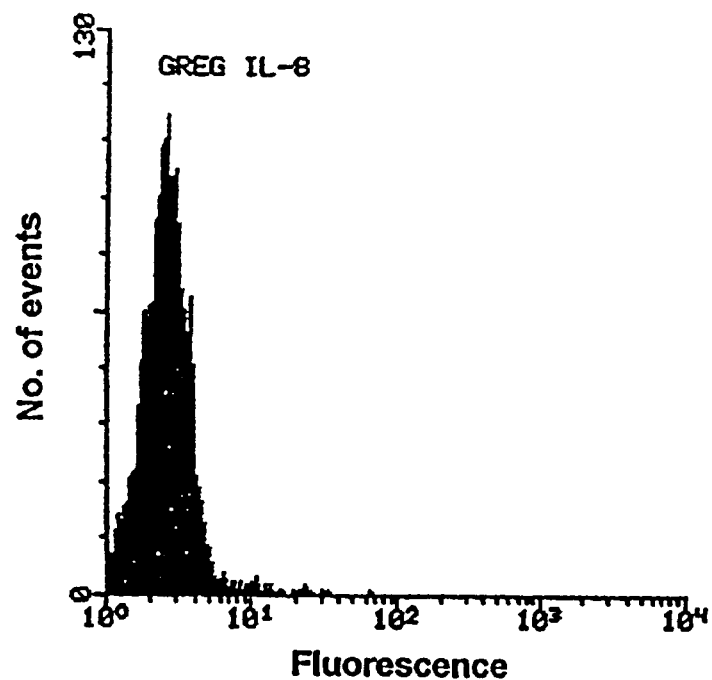
Figure 4B:
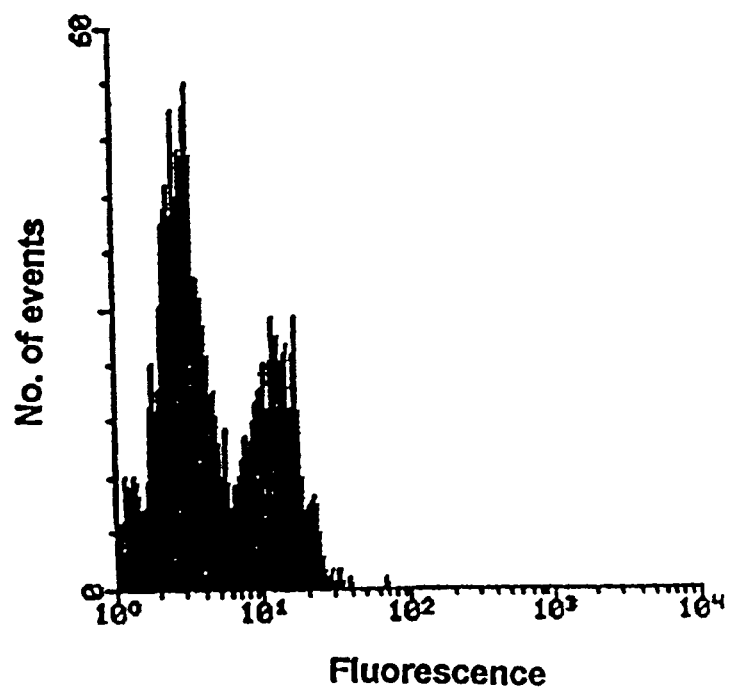
Figure 5A:
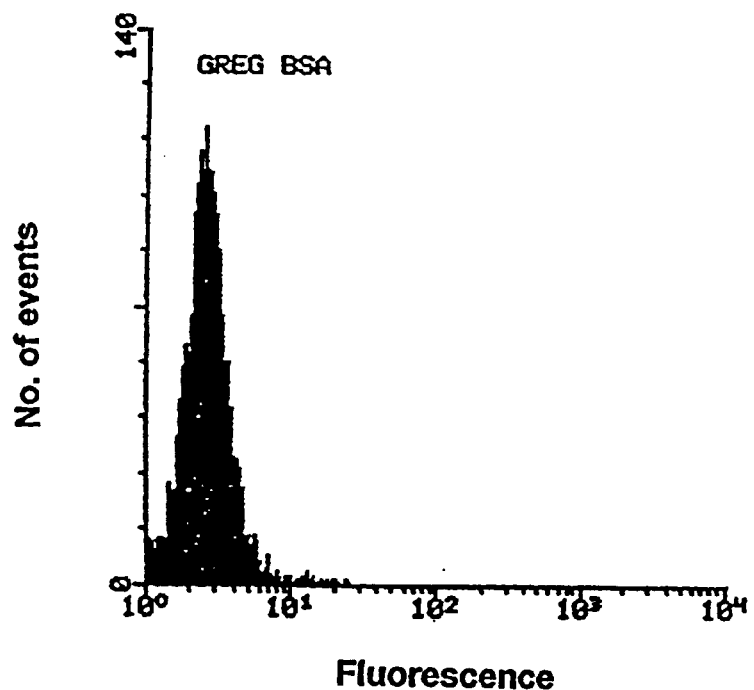
Figure 5B:
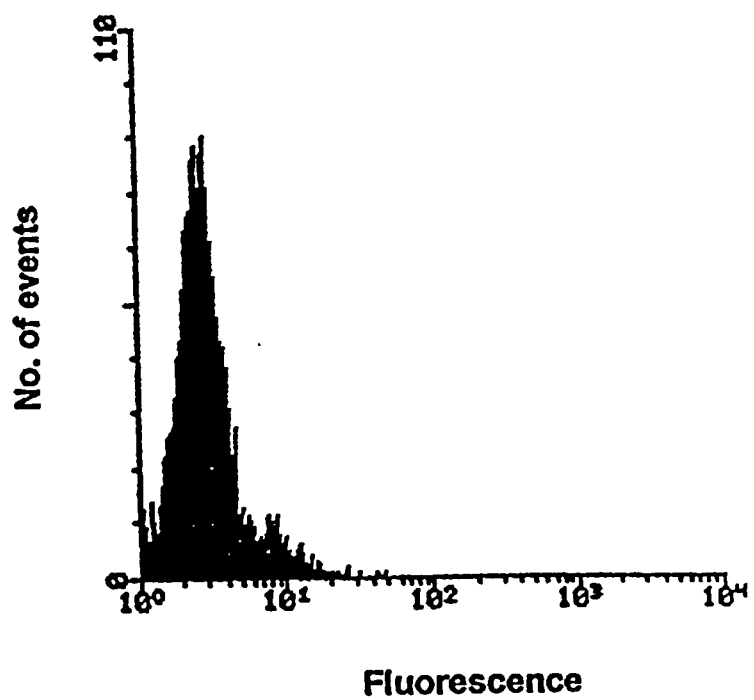
Figure 6A:
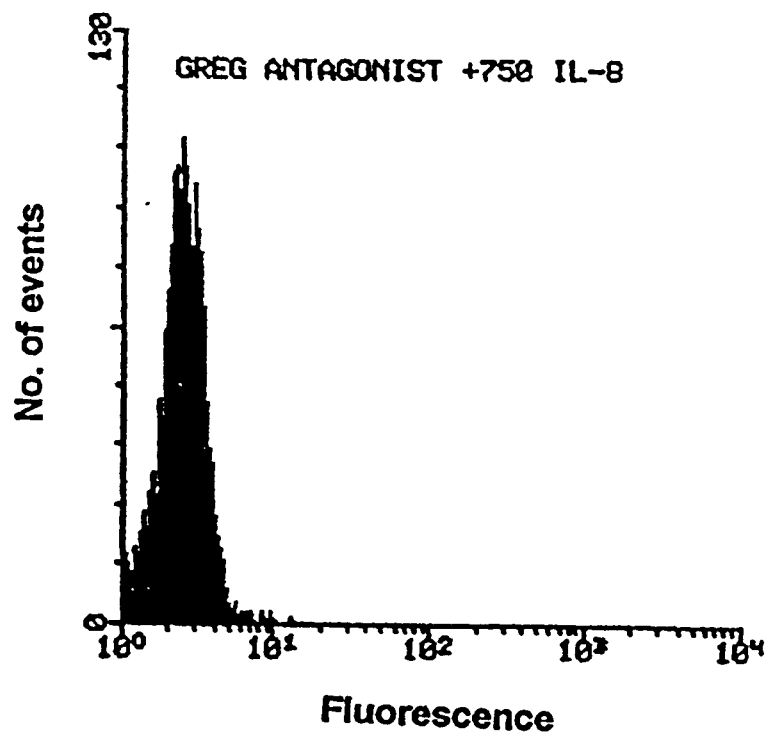
Figure 6B:
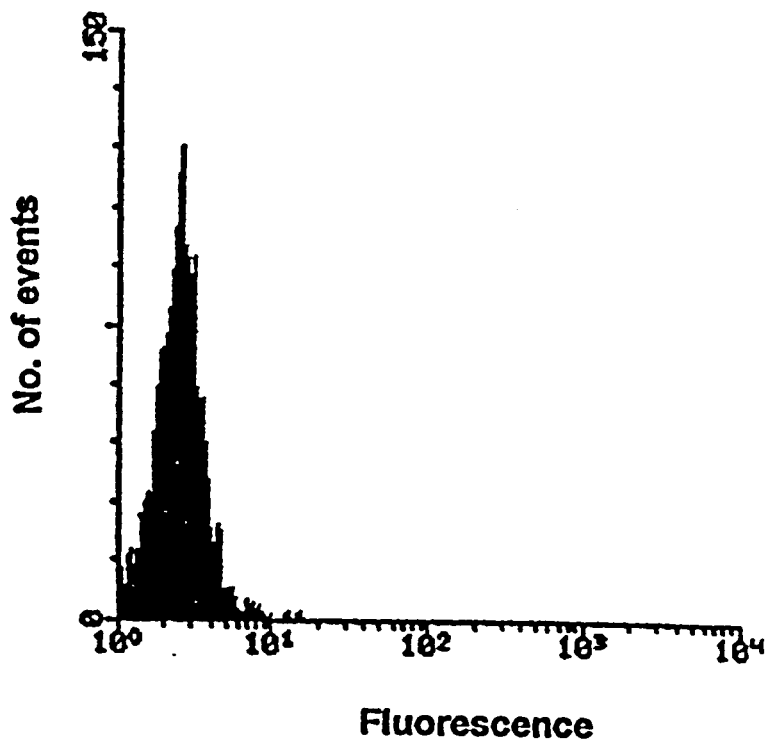

Prior studies of IL-8/NAP-1 have demonstrated that this cytokine induces an increase in Ca after stimulation of neutrophils. FIG. 4 demonstrates the effect of 77 amino acid IL-8 at $10^{-6}M$ on neutrophil Ca release as described above 77 amino acids IL-8/NAP-1 led to increases of arbitrary fluorescence units as compared to excipient treated Fluo-3 loaded neutrophils as shown in FIG. 5. However, as shown in FIG. 6, when the PMN's were pre-incubated with Analog 1 at $10^{-6}M$ they blocked the Ca signal transduction induced by IL-8 as shown in FIG. 4.

EXAMPLE VI

Chemokines form a superfamily that is divided into two distinct functional classes: alpha and beta. Al the members of each class share an organizing primary sequence motif. Alpha family members are distinguished by the C-X-C motif—where the first two cysteines of the motif are separated by an intervening residue. C-X-C chemokines are potent chemoattractats and activators for neutrophils. The beta family chemokines have a C—C motif and are equally potent chemoattractants and activators of monocytes. However, other roles are rapidly emerging for chemokines as well. Thus, both alpha and beta chemokines, have been shown to attract both memory T-cell and eosinophils as well as trigger the release of histamine from basophils.

Edgington, discussed in Bio/technology (1993, 11:676) the potential to design site specific inhibitors and/or agonists for the chemokines. He states that most researchers believe that the greatest promise lies in creating low molecular weight peptide analogs that will compete with natural molecules for the chemokine binding sites. Because both the ligand and the receptor binding site are relatively small, drug designers have focused on understanding where the critical contact points lie that turn on the receptor signal transduction machinery. Many of these investigators believe that similarities in sequence will also yield structural similarities.

Dr. Daniel Witt of Repligen, Cambridge, Mass. is quoted in the article as saying "If you have 15 different receptors and you know the crystal structure for two you can expect the structural model will hold true for all." It was suggested that both chimeric ligands and receptors should fold properly and yield data about critical contact points. "As a system, it is about everything you could ask for imposing structural-functional questions" i.e., there is strong homology amongst the receptors and ligands of the chemokines which will facilitate rational drug designs. It is clear that existing drugs have been synthesized which target similar membrane spanning receptors including: histamine inhibitors, beta blockers, and serotonin receptors which have all yielded receptor antagonists to date.

"Receptor promiscuity" presents one problem to drug design of the chemokines. Within chemokine families, individual receptors bind multiple ligands. Determining chemokine structure and function after dispensing with the dogma of one ligand, one receptor is extremely difficult especially when target cells contain an ensemble of receptors on their membrane. For example, there are at least three kinds of chemokine receptors involved in binding the beta chemokines MCP-1, MIP-1α/β and RANTES. Based on studies to date one receptor binds all three ligands, another binds only MIP-1α/β and a third only binds MCP-1. Similar observations of receptorligand promiscuity are seen with the alpha chemokines. High affinity binding to neutrophils is observed for IL-8; however, evidence for high and low affinity binding receptors is observed with NAP-2, ENA-78 and MGSA. Two closely related neutrophil derived IL-8 receptors, type A and type B, have been cloned whose binding characteristics could account for the binding observed with neutrophils: Type A receptors have a high affinity for IL-8 and low affinity for MGSA and NAP-2. The type B receptors bind IL-8 and MGSA with high and NAP-2 with intermediate affinity. However, it remains possible that more than two IL-8 receptors exist and are expressed on neutrophils.

EXAMPLE VII

Platelet factor 4 (PF-4) is carried within the alpha granules of platelets in the form of a non-covalent complex. PF-4 is tetramer of four identical polypeptide chains, each of which contains 70 residues in the human moieties. When released into the plasma from activated platelets, PF-4 attracts white blood cells i.e., neutrophils and monocytes and it's release may be a signal that is involved in inflammation. Other possible functions of PF-4 derive from a strong binding to negatively charged polysaccharides especially heparan and heparin for which it has a dissociation constant of $10^{-7.5}$. The ability of PF-4 to neutralize heparin and related polymers is of general interest because heparin has been shown to interact with over 50 different enzymes to suppress muscle growth and to accelerate angiogenesis in solid tumors. PF-4 has recently been patented as Oncostatin A for its ability to inhibit tumor growth. It has also been shown to reverse immunosuppression in mice.

PF-4 also binds tightly and preferentially to double stranded DNA in vitro. This binding probably does not incur in vivo but it might be an important attribute of several recently discovered growth related proteins which are homologous to PF-4. Members of this class are 1) induced by IFN-γ, 2) constituently overexpressed in Chinese hamster and human cell lines, 3) strongly induced by Rous sarcoma virus and fibroblast cells and 4) over expressed in stimulated leukocytes.

In contrast to many of the other alpha chemokines, PF-4 does not induce comparable neutrophil responses although chemotaxis and exocytosis have been reported with concentrations that were 1000:10000-fold higher than those required for IL-8.

PF-4 crystallizes as a tetramer, although the monomer structure is similar to that of IL-8. In solution, human PF-4 is in equilibrium among monomers, dimers, and tetramers. PF-4 and IL-8 share 35% sequence identity, including the four cysteines. Molecular modeling studies suggest that a similar folding pattern will be found for all members of the C-X-C family. Even MCP which belongs to the C—C family (beta chemokine), has been found to have the same tertiary structure.

EXAMPLE VIII

Platelet basic protein (PBP) is a highly specific platelet alpha granular protein that is a precursor of low affinity platelet factor 4 (LA-PF4) and beta thromboglobulin (βTG). These proteins differ only in amino terminal amino acid sequence and isoelectric point. PBP is synthesized by megakaryocytes, contains 94 amino acids and is converted to LA-PF4 which contains 85 amino acid residues within megakaryocyte and platelet granules. βTG itself (81 amino acid residues) as originally described can not be detected in cell lysates prepared using trichloroacetic acid. It probably results from amino terminal cleavage of LA-PF4 or PBP after cell secretion. Production of βTG from PBP and LA-PF4 can be demonstrated in vitro by incubating the platelet release supernatant at 37° C. or by limited cleavage with plasmin or trypsin. The three forms of βTG antigen are immunologically identical when using rabbit polyclonal antibodies. The biological activities of PBP and it's derivatives are not well understood. It has been proposed that LA-PF4 [also referred to as connective tissue activating peptide III (CTAP-III)] is a weak mitogen for connective tissue fibroblasts. It has also been reported that βTG antigen promotes chemotaxis in fibroblasts. In recent studies, it was observed that a cleavage product of βTG called neutrophil activating peptide (NAP-2) was formed in cultured and stimulated mononuclear cells and is a potent activator of human neutrophils. NAP-2 is a 78 amino acid peptide corresponding to the major carboxy-terminal fragment of βTG. It has 46% homology with NAP-1/IL-8. NAP-2 behaves as a typical chemotactic receptor agonist, including cytosolic free calcium changes, chemotaxis, and exocytosis while PBB, LA-PF4 and PF4 have little such activity. It should be noted, as discussed above, that it also interacts with the NAP-1/IL-8 receptors.

EXAMPLE IX

IP-10 was originally isolated as a predominate messenger RNA induced by IFN-γ or LPS in monocytes and it's expression has been detected in vivo during the development of a delayed type hypersensitivity cellular immune response by monocytes, endothelial cells, and infiltrating mononuclear cells. In addition, IP-10 expression has been seen in the epidermis, dermis and cutaneous lesions of psoriasis, tuberculoid leprosy, and fixed drug eruptions.

IP-10 is a member of the chemokine superfamily and is approximately 30% homologous to IL-8 and PF-4. Recent studies have shown that IP-10 can elicit an anti-tumor inflammatory response that is capable of inhibiting the growth of plasmacytoma and mammary adenocarcinoma in immunocompetent mice. This effect is thymus dependent suggesting that IP-10 might act on T-cells. In addition, a neutrophil, and monocytic accumulation is seen as a result of IP-10 expression in immunocompetent but not nude mice. IP-10 does not have an ELR motif. ELR incorporation into IP-10 is not sufficient for IL-8 receptor interaction or neutrophil activation and suggests that IP-10 has a different receptor ligand confirmation. However, hybrids formed between IL-8 and IP-10 could be designed which demonstrate that essential receptor binding motifs from the IL-8 sequence could be structured within the IP-10 molecule allowing IL-8 binding.

Recent reports have shown that IP-10 is expressed by activated but not by resting T-hybridoma cells, normal T-cells and thymocytes. While resting lymphocytes did not synthesize IP-10, a high level of IP-10 transcripts are found in lymphoid organs (spleen, thymus, and lymph nodes). Thymic and spleenic stromal cells constitutively express high levels of both IP-10 messenger RNA and protein accounting for the high level of spontaneous expression in lymphoid tissue. Therefore, in addition to its role as a proinflammatory cytokine, IP-10may participate in T-cell effector function of perhaps T-cell development. IP-10 expression has also been shown to be induced in delayed type contact hypersensitivity in sensitized animals.

EXAMPLE X

Human tumors can constitutively express cytokines and growth factors. Melanoma cells constitutively express GRO-α is also termed melanoma growth stimulatory activity. Similarly, GRO-α is expressed in human colon tumors along with GRO-β and GRO-γ. These three genes, GRO-α, GFRO-β, and GRO-γ, are closely linked on chromosome 4. GRO-β and GRO-γ show 90 and 86% sequence homology with GRO-α. The GRO-α/MGSA alpha chemokine has potent chemotactic, growth regulatory and transformative functions. The function of GRO-β and GRO-γ is unknown. GRO-α messenger RNA is selectively overexpressed in psoriasic epidermis and is reduced by therapy with Cyclosporin-A. It has been suggested that this over expression is a karatinocyte response to activated T-cells in psoriasis. GRO-α/MGSA has been localized in a variety of cutaneous lesions. Raised a levels of immunoreactive GRO-α/MGSA in diseased epidermis is detected in verruca vulgaris followed by psoriasis, keratoacanthoma, and squamous cell carcinoma. Detection of GRO-α in basal cell carcinoma is variable being present in the sclerosis variant and absent in the more common nodular variant.

EXAMPLE XI

Recently, another alpha chemokine has been discovered and has been called ENA-78 (epithelial cell derived neutrophil activator). ENA-78 shows significant amino acid sequence homology with NAP-2 (53%), GRO-α (52%), and IL-8 (22%). ENA-78 appears to activate neutrophils through the IL-8 receptor. ENA-78 has been cloned in pigs and was initially described as alveolar macrophage derived chemotactic factor 2. It shares 53% sequence homology with human NAP-2 and 61% sequence homology with the GRO-related proteins. It also has 67% sequence homology with the 78 amino acid ENA-78 and is felt to represent the porcine variant thereof. ENA-78 was initially identified in the conditioned medium of stimulated human epithelial cell line A549. It is produced in response to stimulation with either IL-1β or TNF-α_αυδ_is produced and secreted concomitantly with IL-8, GRO-α, and GRO-γ. ENA-78 consists of 78 amino acids and has a molecular weight of 8357. The four are positioned identically to those of IL-8 and similar analogues. ENA-78 stimulates neutrophils, induces chemotaxis, a rise in intracellular-free Ca and exocytosis. Cross desensitization experiments indicate that ENA-78 acts through the same type of receptors as IL-8, NAP-2 and GRO-α.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

What is claimed is:

1. A peptide having antagonistic activity for alpha chemokines, and having the formula of SEQ. ID NO. 11 which is:

Arg-Cys-Xaa$_1$-Cys-Xaa$_2$-Xaa$_3$-Xaa$_4$-Xaa$_5$-Xaa$_6$-Xaa$_7$-Xaa$_8$-Xaa$_9$-Xaa$_{10}$-Xaa$_{11}$-Xaa$_{12}$ wherein Xaa$_1$ is Gln, Met, Val, Leu, or Thr;

Xaa$_2$ is Ile, Leu, or Val;

Xaa$_3$ is Lys, Gln, or Ser;

Xaa$_4$ is Thr, or Ile;

Xaa$_5$ is Tyr, Thr, Leu, Met, Val, or His;

Xaa$_6$ is Ser, Gln, Ala, or Thr;

Xaa$_7$ is Lys, Arg, Gly, Val, or His;

Xaa$_8$ is Phe, Gly, Ile, His, Val, or Pro;

Xaa$_9$ is absent or is Ile, Val, His, Leu, or Phe;

Xaa$_{10}$ is absent or is His, Pro, Leu, Phe, Arg or Lys;

Xaa$_{11}$ is absent or is Pro, Lys, Phe, or Leu;

Xaa$_{12}$ is absent or is Lys, Arg, or His; said peptide optionally having additional amino acids at the carboxyl terminus, the number of said additional amino acids being less than 10, and optionally an additional two non-polar amino acids at the amino terminus, said peptide being without Glu-Leu at the amino terminus thereof.

2. The peptide of claim 1, wherein one cysteine is substituted by an amino acid selected from the group consisting of: alpha aminobutyric acid, homocysteine or diaminosuberic acid.

3. The peptide of claim 1, wherein both cysteines are substituted by an amino acid selected from the group consisting of: aminobutyric acid, homocysteine or diaminosuberic acid.

4. The peptide of claim 1, wherein said peptide is SEQ. ID NO. 1, which is

Arg-Cys-Gln-Cys-Ile-Lys-Thr-Tyr-Ser-Lys-Pro-Phe-His-Pro-Lys.

5. The peptide of claim 1, wherein said peptide is SEQ. ID NO. 2, which is

Arg-Cys-Gln-Cys-Leu-Gln-Thr-Leu-Gln-Gly-Ile-His-Pro-Lys.

6. The peptide of claim 1, wherein said peptide SEQ. ID NO. 3 which is

Arg-Cys-Gln-Cys-Leu-Gln-Thr-Leu-Gln-Gly-His-Leu-Lys.

7. The peptide of claim 1, wherein said peptide is SEQ. ID NO. 4 which is

Arg-Cys-Gln-Cys-Leu-Gln-Thr-Met-Thr-Gly-Val-His-Leu-Lys.

8. The peptide of claim 1, wherein said peptide is SEQ. ID NO. 5, which is

Arg-Cys-Gln-Cys-Leu-Gln-Thr-Leu-Gln-Gly-His-Leu-Lys.

9. The peptide of claim 1, wherein said peptide is SEQ. ID No. 6, which is

Arg-Cys-Met-Cys-Ile-Lys-Thr-Thr-Ser-Gly-Ile-His-Pro-Lys.

10. The peptide of claim 1, wherein said peptide is SEQ. ID NO. 7, which is

Arg-Cys-Gln-Cys-Ile-Ser-Thr-His-Ser-Lys-Phe-Ile-His-Pro-Lys.

11. The peptide of claim 1, wherein said peptide is SEQ. ID NO. 8, which is

Arg-Cys-Gln-Cys-Ile-Lys-Thr-Tyr-Ser-Lys-Pro-Phe-His-Pro-His.

12. The peptide of claim 1, wherein said peptide is SEQ. ID NO. 9, which is

Arg-Cys-Gln-Cys-Leu-Gln-Thr-Val-Ala-Cly-Ile-His-Phe-Lys.

13. The peptide of claim 1, wherein said peptide is SEQ. ID NO. 10, which is

Arg-Cys-Val-Cys-Leu-Gln-Thr-Thr-Gln-Val-Gly-His-Pro-Lys.

14. The peptide of claim 1, wherein said amino acid sequence further comprises one non-polar amino acid at the N-terminal end.

15. The peptide of claim 1, wherein said amino acid sequence further comprises two non-polar amino acids at the N-terminal end.

16. The peptide of claim 1, wherein said amino acid sequence further comprises additional amino acids at the C-terminal end the number of said additional amino acids being less than 10.

17. A pharmaceutical composition comprising said peptide of claim 1 combined with a pharmaceutically acceptable carrier.

18. A method for the treatment of inflammatory symptoms of arthritis, IBD, SLE, and psoriasis in a patient in need of such treatment, said treatment comprising the administration of the peptide of claim 1.

19. The method as claimed in claim 18 wherein said peptide is combined with other agents to treat said inflammatory symptoms said agent being selected from the group consisting of NSAIDs, steroids, cytotoxic drugs, or cyclosporin-A.

* * * * *

```
                            SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 15 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 4..6
         (D) OTHER INFORMATION: /note= "The cysteine residues in
             the peptide may be substituted with aminobutyric acid,
             homocysteine, or diaminosuberic acid."

(xi) SEQUENCE DESCRIPTION: SEQ ID NO:1:

Arg Cys Gln Cys Ile Lys Thr Tyr Ser Lys Pro Phe His Pro Lys
    1               5                   10                  15

(2) INFORMATION FOR SEQ ID NO:2:

(i) SEQUENCE CHARACTERISTICS:
         (A) LENGTH: 14 amino acids
         (B) TYPE: amino acid
         (C) STRANDEDNESS: Not Relevant
         (D) TOPOLOGY: Not Relevant (ii) MOLECULE TYPE: peptide (iii) HYPOTHETICAL: NO (iv) ANTI-SENSE: NO (ix) FEATURE:
         (A) NAME/KEY: Modified-site
         (B) LOCATION: 4..6
         (D) OTHER INFORMATION: /note= "The cysteine residues
             may be substituted with aminobutyric acid, homocysteine,
             or diaminosuberic acid."

(xi) SEQUENCE DESCRIPTION: SEQ ID NO:2:

Arg Cys Gln Cys Leu Gln Thr Leu Gln Gly Ile His Pro Lys
1               5                   10

(2) INFORMATION FOR SEQ ID NO:3:
```

(i) SEQUENCE CHARACTERISTICS:
            (A) LENGTH: 13 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 4..6
            (D) OTHER INFORMATION: /note= "The cysteine residues
                may be substituted with aminobutryic acid, homocysteine,
                or diaminosuberic acid."

(xi) SEQUENCE DESCRIPTION: SEQ ID NO:3:

Arg Cys Gln Cys Leu Gln Thr Leu Gln Gly His Leu Lys
    1               5                   10

(2) INFORMATION FOR SEQ ID NO:4:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 4..6
            (D) OTHER INFORMATION: /note= "The cysteine residues
                may be substituted with aminobutyric acid, homocysteine
                or diaminosuberic acid."

(xi) SEQUENCE DESCRIPTION: SEQ ID NO:4:

Arg Cys Gln Cys Leu Gln Thr Met Thr Gly Val His Leu Lys
    1               5                   10

(2) INFORMATION FOR SEQ ID NO:5:

(i) SEQUENCE CHARACTERISTICS:
            (A) LENGTH: 13 amino acids
            (B) TYPE: amino acid
            (C) STRANDEDNESS: Not Relevant
            (D) TOPOLOGY: Not Relevant (ii) MOLECULE TYPE: peptide (iii) HYPOTHETICAL: NO (iv) ANTI-SENSE: NO (ix) FEATURE:
            (A) NAME/KEY: Modified-site
            (B) LOCATION: 4..6
            (D) OTHER INFORMATION: /note= "The cysteine residues
                may be substituted with aminobutyric acid, homocysteine,
                or diaminosuberic acid."

(xi) SEQUENCE DESCRIPTION: SEQ ID NO:5:

Arg Cys Gln Cys Leu Gln Thr Leu Gln Gly His Leu Lys
    1               5                   10

(2) INFORMATION FOR SEQ ID NO:6:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The cysteine residues
            may be substituted with aminobutyric acid, homocysteine,
            or diaminosuberic acid."

(xi) SEQUENCE DESCRIPTION: SEQ ID NO:6:

Arg Cys Met Cys Ile Lys Thr Thr Ser Gly Ile His Pro Lys
    1            5                    10

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The cysteine residues
            may be substituted with aminobutyric acid, homocysteine,
            or diaminosuberic acid."

(xi) SEQUENCE DESCRIPTION: SEQ ID NO:7:

Arg Cys Gln Cys Ile Ser Thr His Ser Lys Phe Ile His Pro Lys
    1            5                    10                15

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The cysteine residues
            may be substituted with aminobutyric acid, homocysteine
            or diaminosuberic acid."

(xi) SEQUENCE DESCRIPTION: SEQ ID NO:8:

Arg Cys Gln Cys Ile Lys Thr Tyr Ser Lys Pro Phe His Pro His
    1            5                    10                15

(2) INFORMATION FOR SEQ ID NO:9:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The cysteine residues
            may be substituted with aminobutyic acid, homocysteine
            or diaminosuberic acid."

(xi) SEQUENCE DESCRIPTION: SEQ ID NO:9:

```
Arg Cys Gln Cys Leu Gln Thr Val Ala Gly Ile His Phe Lys
1               5                   10
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 4..6
        (D) OTHER INFORMATION: /note= "The cysteine residues
            may be substituted with aminobutyric acid, homocysteine
            of diaminosuberic acid."

(xi) SEQUENCE DESCRIPTION: SEQ ID NO:10:

```
Arg Cys Val Cys Leu Gln Thr Thr Gln Val Gly His Pro Lys
1               5                   10
```

(2) INFORMATION FOR SEQ ID NO:11:

(i) SEQUENCE CHARACTERISTICS:
        (A) LENGTH: 26 amino acids
        (B) TYPE: amino acid
        (C) STRANDEDNESS: Not Relevant
        (D) TOPOLOGY: Not Relevant (ii) MOLECULE TYPE: peptide (iii) HYPOTHETICAL: NO (iv) ANTI-SENSE: NO (ix) FEATURE:
        (A) NAME/KEY: Modified-site
        (B) LOCATION: 1
        (D) OTHER INFORMATION: /label= Xaa
            /note= "Xaa in the first position may be absent or may be
              any non-polar amino acid."

(ix) FEATURE:
        (A) NAME/KEY: Modified-site
        (B) LOCATION: 2
        (D) OTHER INFORMATION: /label= Xaa -continued /note= "Xaa in the second position may be absent or may be
any non-polar amino acid."

(ix) FEATURE:
    (A) NAME/KEY: Modified-site
    (B) LOCATION: 5
    (D) OTHER INFORMATION: /label= Xaa
        /note= "Xaa in the fifth position may be Gln, Leu, Thr,
        Met, or Val. The cysteine residues may be substituted
        for aminobutyric acid, homocysteine, or diaminosuberic
        acid."

(ix) FEATURE:
    (A) NAME/KEY: Modified-site
    (B) LOCATION: 7
    (D) OTHER INFORMATION: /label= Xaa
        /note= "Xaa in the seventh position may be Ile, Val, or
        Leu."

(ix) FEATURE:
    (A) NAME/KEY: Modified-site
    (B) LOCATION: 8
    (D) OTHER INFORMATION: /label= Xaa
        /note= "Xaa in the eighth position may be Lys, Gln, or
        Ser."

(ix) FEATURE:
    (A) NAME/KEY: Modified-site
    (B) LOCATION: 9
    (D) OTHER INFORMATION: /label= Xaa
        /note= "Xaa at the ninth position may be Thr or Ile."

(ix) FEATURE:
    (A) NAME/KEY: Modified-site
    (B) LOCATION: 10
    (D) OTHER INFORMATION: /label= Xaa
        /note= "Xaa at the tenth position may be Tyr, Thr, His,
        Leu, Met, or Val."

(ix) FEATURE:
    (A) NAME/KEY: Modified-site
    (B) LOCATION: 11
    (D) OTHER INFORMATION: /label= Xaa
        /note= "Xaa in the eleventh position may be Ser, Gln, Thr
        or Ala."

(ix) FEATURE:
    (A) NAME/KEY: Modified-site
    (B) LOCATION: 12
    (D) OTHER INFORMATION: /label= Xaa
        /note= "Xaa at position 12 may be Lys, Arg, His, Val or
        Gly."

(ix) FEATURE:
    (A) NAME/KEY: Modified-site
    (B) LOCATION: 13
    (D) OTHER INFORMATION: /label= Xaa1
        /note= "Xaa position 13 may be Phe, Gly, Ile,
        Val, His or Pro."

(ix) FEATURE:
    (A) NAME/KEY: Modified-site
    (B) LOCATION: 14
    (D) OTHER INFORMATION: /label= Xaa
        /note= "Xaa at position 14 may be absent or may be Ile,
        Val, His, Leu or Phe."

(ix) FEATURE:
    (A) NAME/KEY: Modified-site
    (B) LOCATION: 15
    (D) OTHER INFORMATION: /label= Xaa
        /note= "Xaa at position 15 may be absent or may be His,
        Pro, Leu, Phe, Arg or Lys."

(ix) FEATURE:
    (A) NAME/KEY: Modified-site
    (B) LOCATION: 16
    (D) OTHER INFORMATION: /label= Xaa
        /note= "Xaa at position 16 may be absent or may be Pro,
        Phe, Lys or Leu."

```
        (ix) FEATURE:
              (A) NAME/KEY: Modified-site
              (B) LOCATION: 17
              (D) OTHER INFORMATION: /label= Xaa
                  /note= "Xaa at position 17 may be absent or may be Lys,
                  Arg or His."

(ix) FEATURE:
              (A) NAME/KEY: Modified-site
              (B) LOCATION: 18
              (D) OTHER INFORMATION: /label= Xaa
                  /note= "Xaa at position 18 may be absent or may be any
                  amino acid."

(ix) FEATURE:
              (A) NAME/KEY: Modified-site
              (B) LOCATION: 19
              (D) OTHER INFORMATION: /label= Xaa
                  /note= "Xaa at position 19 may be absent or may be any
                  amino acid."

(ix) FEATURE:
              (A) NAME/KEY: Modified-site
              (B) LOCATION: 20
              (D) OTHER INFORMATION: /label= Xaa
                  /note= "Xaa at position 20 may be absent or may be any
                  amino acid."

(ix) FEATURE:
              (A) NAME/KEY: Modified-site
              (B) LOCATION: 21
              (D) OTHER INFORMATION: /label= Xaa
                  /note= "Xaa at position 21 may be absent or may be any
                  amino acid."

(ix) FEATURE:
              (A) NAME/KEY: Modified-site
              (B) LOCATION: 22
              (D) OTHER INFORMATION: /label= Xaa
                  /note= "Xaa at position 22 may be absent or may be any
                  amino acid."

(ix) FEATURE:
              (A) NAME/KEY: Modified-site
              (B) LOCATION: 23
              (D) OTHER INFORMATION: /label= Xaa
                  /note= "Xaa at position 23 may be absent or may be any
                  amino acid."

(ix) FEATURE:
              (A) NAME/KEY: Modified-site
              (B) LOCATION: 24
              (D) OTHER INFORMATION: /label= Xaa
                  /note= "Xaa at position 24 may be absent or may be any
                  amino acid."

(ix) FEATURE:
              (A) NAME/KEY: Modified-site
              (B) LOCATION: 25
              (D) OTHER INFORMATION: /label= Xaa
                  /note= "Xaa at position 25 may be absent or may be any
                  amino acid."

(ix) FEATURE:
              (A) NAME/KEY: Modified-site
              (B) LOCATION: 26
              (D) OTHER INFORMATION: /label= Xaa
                  /note= "Xaa at position 26 may be absent or may be any
                  amino acid."

(xi) SEQUENCE DESCRIPTION: SEQ ID NO:11:

Xaa Xaa Arg Cys Xaa Cys Xaa Xaa Xaa Xaa Xaa Xaa Xaa Xaa Xaa
    1               5                   10                  15

Xaa Xaa Xaa Xaa Xaa Xaa Xaa Xaa Xaa Xaa Xaa
                    20                  25
```